United States Patent [19]

Renner et al.

[11] Patent Number: 5,075,456
[45] Date of Patent: Dec. 24, 1991

[54] SUBSTITUTED, UNSATURATED, BIREACTIVE BICYCLE IMIDES AND THE USE THEREOF

[75] Inventors: Alfred Renner, Muntelier; Christian Vonlanthen, Ependes, both of Switzerland; Edward Irving, Higher Whitley; Christopher P. Banks, Saffron Walden, both of England

[73] Assignee: Ciba-Geigy Corporation, Ardsley, N.Y.

[21] Appl. No.: 485,685

[22] Filed: Feb. 27, 1990

[30] Foreign Application Priority Data

Mar. 7, 1989 [CH]  Switzerland ............................ 829/89

[51] Int. Cl.[5] ........................ C07D 209/76; C08F 2/46
[52] U.S. Cl. .................................... 548/435; 526/262
[58] Field of Search .................. 548/435; 526/262, 155

[56] References Cited

U.S. PATENT DOCUMENTS

| | | | |
|---|---|---|---|
| 4,440,850 | 4/1984 | Paul et al. | 548/435 |
| 4,515,962 | 5/1985 | Renner | 548/435 |
| 4,604,437 | 8/1986 | Renner | 548/435 |
| 4,667,003 | 5/1987 | Renner | 548/435 |
| 4,709,047 | 11/1987 | Renner et al. | 548/435 |
| 4,728,742 | 3/1988 | Renner | 548/435 |
| 4,742,166 | 5/1988 | Renner | 548/435 |
| 4,966,923 | 10/1990 | Banks et al. | 528/262 |

FOREIGN PATENT DOCUMENTS 0269568 6/1988 European Pat. Off. .

Primary Examiner—Mukund J. Shah
Assistant Examiner—E. C. Ward
Attorney, Agent, or Firm—JoAnn Villamizar

[57] ABSTRACT

Imides of the formula I

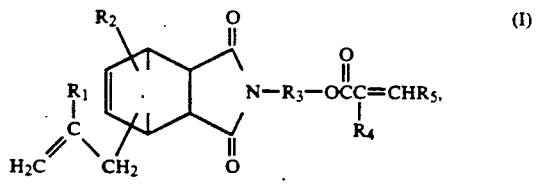

In which $R_1$, $R_2$ and $R_4$ independently of one another are hydrogen or methyl, $R_3$ is a direct bond or a $C_2$–$C_{20}$aliphatic radical which can be interrupted by O atoms or a mononuclear or polynuclear $C_5$–$C_{20}$cycloaliphatic or $C_6$–$C_{20}$aromatic radical or is a group of the formula II

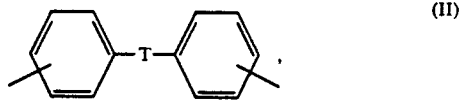

in which T is methylene, isopropylidene, CO, O, S or $SO_2$ and $R_5$ is hydrogen or phenyl, can be crosslinked either photochemically or by heat and produce polymers having excellent properties, in particular a very high resistance to heat. They are particularly suitable for the production of heat-resistant photolithographs or as matrix resins for the production of composite materials.

3 Claims, No Drawings

SUBSTITUTED, UNSATURATED, BIREACTIVE BICYCLE IMIDES AND THE USE THEREOF

The invention relates to bicyclo[2.2.1]hept-5-ene-2,3-dicarboximides which are substituted by allyl or methallyl groups and also by acryloyloxy, methacryloyloxy or cinnamoyloxy groups, to their preparation, to the polymers obtainable therefrom by heating or by photopolymerization and to the use of the said imides as photoresists or as matrix resins for the preparation of prepregs.

U.S. Pat. No. 4,515,962 and 4,742,166 describe allyl-substituted or methallyl-substituted bicyclo[2.2.1]hept-5-ene-2,3-dicarboximides and the polymers obtainable therefrom by heating.

U.S. Pat. No. 4,728,742 describes allyl-substituted or methallyl-substituted bicyclo[2.2.1]hept-5-ene-2,3-dicarboximides containing hydroxyl groups and the polymers obtainable therefrom by heating, if appropriate in the presence of other comonomers.

U.S. Pat. No. 4,709,047 describes allyl-substituted or methallyl-substituted bicyclo[2.2.1]hept-5-ene-2,3-dicarboximides containing sulfonyloxy groups and the use thereof as catalysts for the thermal crosslinking of cationically polymerizable monomers.

U.S. Pat. No. 4,440,850 describes a process for the production of images in which compounds containing in the same molecule both an acryloyl or methacryloyl group and a substituted or unsubstituted bicyclo[2.2.1-]hept-5-en-2-yl or 7-oxabicyclo[2.2.1]hept-5-en-2-yl group are employed as a photoresist. These can be esters of bicycloheptene monocarboxylic acid, monoesters or diesters of bicycloheptene dicarboxylic acid and imides of the last-mentioned acid. The bicycloheptenyl groups can be unsubstituted or can contain one to four methyl groups or an allyl group as substituents.

Allyl-substituted bicyclo[2.2.1]hept-5-ene-2,3-dicarboximides are not specifically disclosed in U.S. Pat. No. 4,440,850. The compounds used in the process according to U.S. Pat. No. 4,440,850 are polymerized solely by the action of actinic radiation. Polymerization of these compounds by heating is not mentioned there.

The present invention relates to imides of the formula I

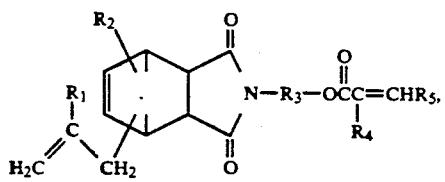

in which $R_1$, $R_2$ and $R_4$ independently of one another are hydrogen or methyl, $R_3$ is a direct bond or a $C_2$-$C_{20}$ aliphatic radical which can be interrupted by O atoms or a mononuclear or polynuclear $C_5$-$C_{20}$ cycloaliphatic or $C_6$-$C_{20}$ aromatic radical or is a group of the formula II

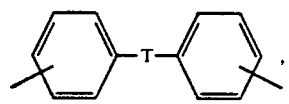

in which T is methylene, isopropylidene, CO, O, S or $SO_2$ and $R_5$ is hydrogen or phenyl.

Surprisingly, in spite of the accumulation of very reactive double bonds, the compounds according to the invention can be prepared in a pure state by distillation and can be processed without premature gelling.

The imides according to the invention are bireactive monomers which can be polymerized either by the action of actinic radiation or by heat. The crosslinked polymers thus obtained are distinguished in particular by a high glass transition temperature and a high resistance to heat. The invention therefore also relates to polymers which are obtainable by heating an imide of the formula I for 6 to 60 hours at a temperature between 180° and 300° C., preferably between 200° and 250° C., and to polymers which are obtainable by exposing an imide of the formula I to actinic radiation, if appropriate in the presence of a photoinitiator.

Preferred imides, according to the invention, of the formula I are those in which $R_1$ and $R_2$ are each hydrogen.

The radical

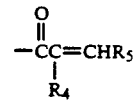

in the imides according to the invention originates from the corresponding unsaturated carboxylic acid, preferably cinnamic acid, methacrylic acid or especially acrylic acid. Preferred imides of the formula I are therefore those in which $R_4$ is hydrogen and $R_5$ is phenyl or imides in which $R_5$ is hydrogen and $R_4$ is methyl or preferably hydrogen.

$R_3$ can be a divalent, linear or branched aliphatic radical having 2-20, preferably 2-10 and especially 2-6 C atoms the chain of which can be interrupted by one or more oxygen atoms. Examples of suitable aliphatic radicals $R_3$ are ethylene, 1,2-propylene, 1,3-propylene, butylene, pentamethylene, hexamethylene, heptylene, octylene, decylene, dodecylene, hexadecylene or neopentylene. Aliphatic radicals interrupted by oxygen atoms can, for example, be derived from ethylene glycol or from 1,2-propylene glycol or 1,3-propylene glycol and can correspond to groups of the formulae

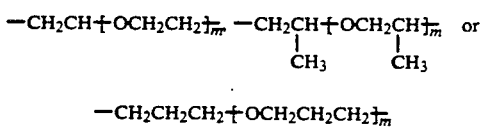

in which m=1-8.

If $R_3$ is derived from ethylene glycol, m is suitably 1-8, in particular 1-4. If $R_3$ is derived from propylene glycol, m is, for example, 1-5, in particular 1-3.

$R_3$ can also be a mononuclear or polynuclear, cycloaliphatic, divalent radical having 5-20 C atoms, for example cyclopentylene, cyclohexylene, cycloheptylene, cyclooctylene, bis(cyclohexylene)methane, 2,2-bis(cyclohexylene)propane and decalinylene. Cyclohexylene, particularly 1,4-cyclohexylene, is particularly preferred.

If $R_3$ is an aromatic radical, it is preferably 1,3-phenylene, 1,4-phenylene or naphthylene each of which can, if desired, also be substituted by one or more $C_{1-4}$ alkyl groups, such as methyl, ethyl or propyl. The said groups are preferably unsubstituted. 1,3-phenylene and 1,4-phenylene groups are particularly preferred as aromatic radicals.

If $R_3$ is a group of the formula II, T is preferably O, $SO_2$, methylene or isopropylidene.

Imides of the formula I which are particularly preferred are those in which $R_3$ is a direct bond, a $C_2$-$C_{10}$aliphatic radical or a group

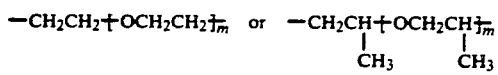

in which m=1 or 2, a $C_5$-$C_6$cycloaliphatic radical or a $C_6$-$C_{10}$aromatic radical or a group of the formula II in which T is methylene or isopropylidene.

Imides of the formula I which are very particularly preferred are those in which $R_3$ is a direct bond, the radical —$CH_2CH_2$—,

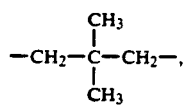

—$CH_2CH_2OCH_2CH_2$—, 1,3-cyclohexylene, 1,4-cyclohexylene, 1,3-phenylene or 1,4-phenylene.

The most preferred imides of the formula I are those in which $R_1$, $R_2$ and $R_5$ are each hydrogen, $R_3$ is a direct bond or the radical —$CH_2CH_2$— and $R_4$ is hydrogen or methyl, and particularly the imide of the formula I in which $R_1$, $R_2$, $R_4$ and $R_5$ are each hydrogen and $R_3$ is the radical —$CH_2CH_2$—.

The imides according to the invention can be prepared in a manner known per se, for example by reacting an imide of the formula III, containing hydroxyl groups,

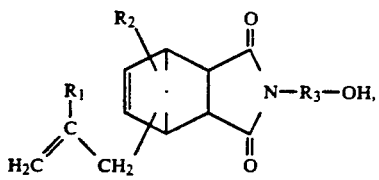

with a compound of the formula IV

in which the radicals $R_1$, $R_2$, $R_3$, $R_4$ and $R_5$ are as defined above and $R_6$ is OH, halogen or $C_1$-$C_4$alkoxy.

Compounds of the formula III and the preparation thereof are described in U.S. Pat. No. 4,728,742. Compounds of the formula IV are known and are commercially available. If $R_6$ is halogen, the corresponding acid bromides and especially chlorides are preferred. If $R_6$ is an alkoxy group $OR_7$, the methyl ester is preferred.

Suitable reaction conditions for the esterification of alcohols or phenols with ester-forming acid derivatives, such as the compounds of the formula IV, are known to those skilled in the art. If free carboxylic acids or carboxylic acid esters of the formula IV are employed in the esterification of the compounds of the formula III, the reaction mixture is preferably heated under reflux, the water or alcohol formed in the reaction being distilled off during the reaction, if appropriate in the form of an azeotrope with the solvent.

If the esterification of the imide of the formula III containing hydroxyl groups is carried out by means of an acid halide of the formula IV, the reaction is preferably carried out with cooling in the presence of an acid acceptor, for example in the presence of tertiary amines, for example triethylamine, pyridine or N,N-dimethylaniline. The last-mentioned reaction of the imides of the formula III with acid halides, in particular acid chlorides, of the formula IV is preferred as a process for the preparation of the compounds according to the invention.

The compounds according to the invention are liquid or low-melting solid substances which are distinguished by a high reactivity and, because of their low viscosity, by easy processing and which can be polymerized to give solid products having a high glass transition temperature. The polymers have a very high resistance to heat and exhibit a very low shrinkage or a low loss in weight at high temperatures.

Thanks to the presence of two different reactive groups, the olefinic double bonds and the acryloyl, methacryloyl or cinnamoyl groups, the imides according to the invention can be used as educts or intermediates for the preparation of various types of polymers. Owing to their low viscosity, the imides according to the invention are also suitable for use as polymerizable solvents or as reactive thinners for unsaturated imide resins. It is, of course, possible to add inert and stable substances, such as fillers, pigments, dyes and other additives, to the imides of the formula I before they are polymerized to give crosslinked structures.

The compounds according to the invention can be used and polymerized without further treatment, or they can first be dissolved in an organic solvent, such as toluene, xylene, methyl ethyl ketone, ethylene glycol monoalkyl and dialkyl ethers having 1–4 C atoms in the alkyl groups or a similar customary solvent. Such solutions can be used as impregnating agents or coating agents or as a means of dispatch to the consumer.

If appropriate, the imides according to the invention can also be polymerized in the presence of other co-polymerizable compounds. Other unsaturated imides, in particular the substituted, unsaturated, bicyclic imides according to U.S. Pat. Nos. 4,515,962 and 4,742,166 are particularly suitable for this purpose. Other suitable copolymerizable compounds are those containing two or more acryloyl or methacryloyl groups, for example reaction products of epoxy resins which can be so-called advanced with stoichiometric amounts of acrylic or methacrylic acid, so that the product contains essentially no more free epoxide groups. Products of this type are sold, for example, by the DOW Chemical Company under the trade name Derakane ®.

If appropriate, curing catalysts can also be added to the imides according to the invention or to mixtures containing these imides. Catalysts which are particularly suitable for thermal crosslinking are the allyl-substituted or methallyl-substituted unsaturated, bicyclic imides containing sulfonyloxy groups described in U.S. Pat. No. 4,709,047, in particular allylbicyclo[2.2.1]hept-5-ene-2,3-dicarboxylic acid N-benzenesulfonyloxyimide. Examples of other suitable catalysts for thermal crosslinking are benzoyl peroxide, t-butyl perbenzoate, cumene hydroperoxide, di-t-butylperoxide, bis-t-butyl-peroxybutane, methyl ethyl ketone hydroperoxide and dicumylperoxide. The concentration of the catalyst which can be used is appropriately between 0.1 and 15.0, preferably between 0.25 and 5.0 and particularly preferably between 0.5 and 2.0, % by weight, relative to the total weight of the imide of the formula I and the other unsaturated imides which may be present in the mixture.

It is preferable to use suitable photoinitiators as the catalyst in the photochemical polymerization of the imides according to the invention. Examples of suitable photoinitiators are α-halogen-substituted acetophenones, such as trichloromethyl-4'-tert-butyl phenyl ketone, α-hydroxy-α-alkyl-substituted acetophenones, such as 2-hydroxy-2-methyl-1-phenylpropan-1-one, 1-hydroxycyclohexyl phenyl ketone, benzoin and alkyl ethers thereof (for example the n-butyl ether), α-methylbenzoin or alkyl esters of α,α-dialkoxy-α-benzoylacetic acid, benzophenones, such as benzophenone itself and 4,4'-bis-(dimethylamino)-benzophenone, O-alkoxycarbonyl derivatives of an oxime of benzil or of 1-phenylpropan-1,2-dione, such as benzil-(O-ethoxycarbonyl) α-monoxime and 1-phenylpropane-1,2-dione-2-(O-ethoxycarbonyl) oxime, benzil ketals, for example the dimethyl ketal thereof, substituted thioxanthones, for example 2-chlorothioxanthone, anthraquinones, esters of phenylglyoxylic acid, 2-benzoyl-2-phenyl-1,3-dioxolanes and 4-benzoyl-4-phenyl-1,3-dioxolanes and also photoredox systems consisting of a mixture of a phenothiazine dye (for example methylene blue) or a quinoxaline (for example a metal salt of 2-(m-or p-methoxyphenyl)-quinoxaline-6'- or 7'-sulfonic acid) together with an electron donor, such as benzene sulfinic acid or another sulfinic acid or a salt thereof, for example the sodium salt, or an arsine, a phosphine or thiourea.

α-Aminoacetophenone derivatives, for example 2-methyl-1-[4-(methylthio)-phenyl]-2-morpholinopropan-1-one, are also suitable photoinitiators. Compounds of this type are described, for example, in U.S. Pat. Nos. 4,318,791, 4,582,862 and 4,739,052. Preferred photoinitiators are benzil dimethyl ketal, 1-hydroxycyclohexyl phenyl ketone and 2-methyl-1-[4-(methylthio)-phenyl]-2-morpholinopropan-1-one. In general, about 0.15 to 10% by weight, preferably about 2.5 to 5% by weight, of photoinitiator are added, relative to the total weight of the imides according to the invention and of the other compounds containing acryloyl or methacryloyl groups which may, if appropriate, be present in the mixture.

Owing to the high reactivity of the imides according to the invention and in view of the fact that they are bireactive monomers, these compounds are suitable for use in a large number of applications, for example as laminating or electrical resins, as high-temperature adhesives or for the preparation of coatings or mouldings, prepregs and composite materials. In this regard it can be advantageous for many applications first to solidify the liquid compounds or mixtures by the action of actinic radiation and then to cause them to react to give crosslinked polymers.

A preferred field of application for the imides of the formula I is their use as photoresists.

The invention therefore also relates to a process for the production of images, which comprises exposing a layer containing an imide of the formula I, applied to a carrier, to actinic radiation imagewise in a predetermined pattern, so that the exposed areas of the layer are photopolymerized, and then developing the image by dissolving the non-polymerized areas of the layer in a solvent.

If desired, the image formed after developing can also be subjected to a subsequent heat treatment, for example by heating at 100°-200° C. for 1-5 hours. Particularly heat-resistant photolithographs in which the loss in weight begins only at temperatures above 400° C. are obtained by this means. The liquid imides of the formula I or the liquid compositions containing them can be applied to suitable carriers by conventional methods, such as spray coating, whirler-coating, application by rolling, cascade coating and, in particular, curtain coating. In a typical case the carrier is coated in such a way that the layer is 1 to 250 μm, preferably 10 to 30 μm, thick. The carrier can consist, for example, of copper, aluminium or another metal, or of paper, synthetic resin or glass.

In the photopolymerization stage of the process according to the invention it is preferable to use actinic radiation of a wavelength of 200-600 nm. Suitable sources of actinic radiation are, inter alia, carbon arcs, mercury vapour arcs, fluorescent tubes containing luminous substances which emit ultraviolet light, argon and xenon incandescent lamps, tungsten lamps and photographic floodlight lamps. Amongst these mercury vapour arcs, in particular sunlight lamps, fluorescent sunlight lamps and metal halide lamps are the most suitable. The times required for the exposure of the imides of the formula I or of the composition containing them depend on various factors, inter alai, for example, the individual compounds used, the nature of the light source and the distance of the latter from the irradiated layer. The times suitable can be determined easily by those skilled in the art who are familiar with photopolymerization methods. For example, the imide or the composition can be irradiated for 1-10 minutes at a distance of 10-100 cm from a source of radiation.

Solvents suitable for developing the image can be found easily by series tests: these are, inter alia, cyclohexanone, trimethylcyclohexanone, ethanol, toluene, 2-ethoxyethanol, 1,1,1-trichloroethane and mixtures thereof. It may be necessary to assist the action of the solvent by stirring or gentle brushing. If the carrier has a layer of a suitable electrically conductive metal, usually copper or silver, in direct contact with the photopolymerized composition, the non-crosslinked polymer can, if appropriate, be removed in order to uncover the metal. Metal uncovered in this way can then be removed by etching by means of etching liquids, such as ferric chloride or ammonium persulfate solutions, at the unexposed areas, in order to form a printed circuit.

Another preferred field of application for the imides according to the invention is their use as matrix resins for composites. The invention therefore also relates to the use of the imides of the formula I for the preparation of prepregs and to a process for the preparation of prepregs, which comprises impregnating a fibrous material with an imide of the formula I or with a mixture containing an imide of the formula I and then exposing the impregnated material to actinic radiation, so that the imide or the mixture containing an imide is solidified by photopolymerization and becomes essentially tack-free, but still remains crosslinkable by heat.

Examples of suitable fibrous material are glass fibre, carbon fibre or aramid fibre fabrics, for example fibrous fabrics composed of the poly-(1,4-phenyleneterephthalamides) which are known under the trade name Kevlar ®.

The following examples illustrate the invention.

PREPARATION EXAMPLES

Example 1

Allylbicyclo[2.2.1]hept-5-ene-2,3-dicarboxylic acid N-(2'-acryloyloxyethyl)-imide Allylbicyclo[2.2.1]hept-5-ene-2,3-dicarboxylic acid N-(2'-hydroxyethyl)-imide is prepared as in Example 2 of U.S. Pat. No. 4,728,742.

370.5 g of this compound and 166.96 g of triethylamine are dissolved in 1200 ml of toluene and the mixture is cooled to 5° C. 135.75 g of acryloyl chloride are added dropwise to this solution, with vigorous stirring and external cooling, at such a rate that the temperature remains between 4° and 7° C. The reaction mixture is then stirred overnight at room temperature, next morning 600 ml of deionized water are added and the pH is adjusted to 4.7 with 1N HCl. The solution is washed with twice 500 ml of water and dried over $Na_2SO_4$ and the toluene is distilled off on a rotary evaporator at 50° C. and 13.3 Pa. This gives 406 g of crude product in the form of a pale brown oil, which corresponds to a yield of 93.8% of theory.

0.5% of methylene blue are added to this crude product as a stabilizer for purification by distillation. Boiling point at 27 Pa: 180°–190° C., yield 380.8 g, corresponding to 84.5% of theory.

| Analysis: | | |
|---|---|---|
| | calculated for $C_{17}H_{19}NO_4$ | found |
| % C: | 67.76 | 67.49 |
| % H: | 6.36 | 6.38 |
| % N: | 4.65 | 4.76 |
| $n_D^{25}$ = | 1.5227 | |
| $\eta_{25}$ = | 650 mPa · s | |

The polymerization of this monomer proceeds with the liberation of 575.75 J/g. In differential thermoanalysis (Mettler TA 3000), a reaction maximum is observed at 164° C., which can be attributed to acrylic polymerization, and also two other maxima at 251° and 295° C., which correspond to the allylnadic group. After polymerization for 6 hours at 250° C., a clear, tough solid having a glass transition temperature of 322° C. is obtained.

Example 2

Allylbicyclo[2.2.1]hept-5-ene-2,3-dicarboxylic acid N-(2'-methacryloyloxyethyl)-imide 123.5 g—of allylbicyclo[2.2.1]hept-5-ene-2,3-dicarboxylic acid N-(2'-hydroxyethyl)-imide (as in Example 2 of U.S. Pat. No. 4,728,742),
150 g—of methyl methacrylate,
0.137 g—of hydroquinone,
0.082 g—of phenothiazine and
1.02 g—of sodium methylate are heated under a column 30 cm in length, packed with rings (d = 3 mm, steel wire). A distillate having a refractive index of 1.4038 and containing 15% of methanol is obtained at an internal temperature of 102° C. An azeotropic mixture composed of 50% of methanol and 50% of methyl methacrylate distilled over at 110° C. ($n_D^{25}$ = 1.3768). After 2 hours of continued esterification, a further 1.02 g of $NaOCH_3$ are added and, after 3.5 hours, a further 0.3 g. A total distillate of 54 g is obtained.

The mixture is then cooled, 200 g of toluene are added and it is extracted by shaking with 200 g of 0.25 N NaOH. The mixture is washed twice with water and dried over $Na_2SO_4$, and the toluene is removed on a rotary evaporator at 60° C. and under reduced pressure, finally at 15 Pa. This gives 125 g of a yellow oil (79.3% of theory) having the following elementary composition:

| | calculated for $C_{18}H_{31}NO_4$ | found |
|---|---|---|
| % C: | 68.55 | 68.35 |
| % H: | 6.71 | 6.73 |
| % N: | 4.44 | 4.49 |

The oil is rectified at 145°–146° C. and 0.4 Pa. Yield of distillate: 73.8%.

$n_D^{25}$ = 1.5211
$\eta_{25}$ = 908 mPa.s 90.68 J/g are liberated at a reaction maximum of 122° C. and 304.58 J/g at a reaction maximum of 290° C. in the course of the thermal polymerization. After curing for 6 hours at 250° C., the $T_G$ is 295° C.

Example 3

Allylbicyclo[2.2.1]hept-5-ene-2,3-dicarboxylic acid N-(2'-cinnamoyloxyethyl)-imide 49.4 g—of allylbicyclo[2.2.1]hept-5-ene-2,3-dicarboxylic acid N-(2'-hydroxyethyl)-imide (as in Example 2 of U.S. Pat. No. 4,728,742),
29.3 g—of cinnamic acid,
0.6 ml—of 50% aqueous hypophosphorous acid and
20 ml—of a mixture of xylene isomers are heated at the boil.

A xylene/water azeotrope is distilled off for 8 hours at 160°–165° C. The water is separated off and the xylene is recycled. After a further 16 hours the mixture is washed with sodium carbonate solution and water and dried over $Na_2SO_4$ and the xylene is then distilled off on a rotary evaporator. This leaves 75 g (=90% of theory) of a pale yellow resin having a viscosity of 2.8 Pa.s at 80° C.

| analysis: | calculated for $C_{23}H_{23}NO_4$ | found |
|---|---|---|
| % C: | 73.19 | 72.68 |
| % H: | 6.14 | 6.24 |
| % N: | 3.71 | 3.71 |

Example 4

Allybicyclo[2.2.1]hept-5-ene-2,3-dicarboxylic acid N-acryloyloxyimide 69.5 g of hydroxylamine hydrochloride are dissolved in water and 204 g of allylbicyclo[2.2.1]hept-5-ene-2,3-dicarboxylic anhydride are added. 80 g of 50% aqueous sodium hydroxide solution are then added dropwise with stirring, the mixture is heated at reflux temperature for 1 hour, all the volatile constituents are then distilled off and the residue is taken up in toluene and freed from undissolved sodium chloride by filtration, and the solvent is removed on a rotary evaporator at 150° C. and 2000 Pa.

129.2 g—of this residue (allylbicyclo[2.2.1]hept-5-ene-2,3-dicarboxylic acid N-hydroxyimide) and
65.7 g—of triethylamine are dissolved in
470.0 g—of toluene. This solution is cooled to 4° C. 53.4 g of acryloyl chloride are added dropwise, with vigorous stirring and external cooling, at such a rate that the temperature remains between 4° and 6° C. The mixture is stirred overnight at room temperature, 200 ml of H$_2$O are then added and the pH is adjusted to a value of 5.4 by means of 60 g of 1N HCl. Working up analogously to Example 1 gives 146.7 g (91% of theory) of a brown oil having the following elementary composition and molecular weight:

|  | calculated for C$_{15}$H$_{15}$O$_4$N: | found |
|---|---|---|
| % C: | 65.92 | 65.80 |
| % H: | 5.53 | 5.62 |
| % N: | 5.13 | 5.13 |
| M$_n$: | 273 | 271 (GCP in THF) |
| M$_w$: |  | 275 |

When a small sample is heated for 12 hours a crosslinked polmer having T$_G$=340° C. is obtained.

Example 5

Allylmethylbicyclo[2.2.1]hept-5-ene-2,3-dicarboxylic acid

N-(2',2'-dimethyl-3'-acryloyloxypropyl)-imide 54.56 g—of allylmethylbicyclo[2.2.1]hept-5-ene-2,3-dicarboxylic anhydride (prepared as in Example 2 of U.S. Pat. No. 3,105,839) and 25.79 g—of neopentanolamine are heated at 130°-150° C. for 3 hours under a descending condenser. In the course of this 4.5 cm$^3$ of H$_2$O distill off. The hydroxyneopentylimide is then rectified at 181°-185° C./13 Pa.

25 g—of the above reaction product and
9.21 g—of triethylamine are dissolved in
60 g—of toluene and the mixture is cooled to 3° C.
7.42 g—of acryloyl chloride are added dropwise, with vigorous stirring and external cooling, at such a rate that the temperature remains between 3° and 7° C. The temperature is then allowed to rise to 20° C. and the mixture is stirred overnight.

The reaction mixture is worked up as described in Example 1 and 29.3 g of a pale brown oil are obtained, which corresponds to a quantitative yield. Rectification in the presence of 0.2% of methylene blue at 167°-168° C./100 Pa gives 11.35 g (34.2% of theory) of a viscous liquid having the following elementary composition and properties:

|  | calculated for C$_{21}$H$_{27}$NO$_4$ | found |
|---|---|---|
| % C: | 70.58 | 69.06 |
| % H: | 7.62 | 7.70 |
| % N: | 3.92 | 4.30 |
| M$_n$: | 357 | 355 (GCP in THF) |
| n$^D_{25}$ = | 1.5081 |  |
| η$_{25}$ = | 2.88 P·s |  |
| Heat of polymerization (DTA): | 420 J/g |  |
| Reaction maxima: | 182° C. (Acryl) |  |
|  | 265° C. ⎫ |  |
|  | 315° C. ⎭ Allylnadic |  |
| Glass transition temperature of the | 202° C. |  |

|  | calculated for C$_{21}$H$_{27}$NO$_4$ | found |
|---|---|---|
| crosslinked polymer: |  |  |

Example 6

Allylbicyclo[2.2.1]hept-5-ene-2,3-dicarboxylic acid

N-(4'-acryloyloxyphenyl)-imide 295 g—of allylbicyclo[2.2.1]hept-5-ene-2,3-dicarboxylic acid N-(4'-hydroxy-phenyl)-imide (prepared as in Example 6 of U.S. Pat. No. 4,728,742) and 106.2 g—of triethylamine are dissolved in
450 g—of toluene.
90.5 g—of acryloyl chloride are added to this solution at 8°-10° C. with vigorous stirring and cooling.

The mixture is left overnight at room temperature to complete the reaction, 400 ml of water are added, the pH is adjusted to 4.0 with 1N HCl, the solution is decanted, washed again with twice 400 ml of H$_2$O and dried over Na$_2$SO$_4$. When the toluene solution is evaporated, a mash of crystals is formed, and this is cooled, suction-drained and washed with heptane. The crystals are dried at 40° C. in vacuo and 298.4 g (85.5% of theory) of the acrylate are obtained, melting point 62°-65° C.

| Elementary analysis | calculated for C$_{21}$H$_{19}$NO$_4$: | found |
|---|---|---|
| % C: | 72.19 | 71.92 |
| % H: | 5.48 | 5.55 |
| % N: | 4.01 | 3.88 |
| M$_n$: | 349 | 354 (GPC in THF) |

A polymer prepared at 250° C. has a glass transition temperature of 262° C.

Example 7

Allylbicyclo[2.2.1]hept-5-ene-2,3-dicarboxylic acid

N-[2'-(2''-hydroxyethoxy)ethyl]-imide 81.6 g—of allylbicyclo[2.2.1]hept-5-ene-2,3-dicarboxylic anhydride and 42 g—of diglycolamine [2-(2'-aminoethoxy)ethanol] are subjected to condensation for 4.5 hours and the mixture is distilled (boiling point 196°-197° C. at 1.6 Pa). Yield, 89.3 g of the corresponding hydroxyethoxyethylimide.

25 g—of the above intermediate (prepared as in Example 4 of U.S. Pat. No. 4,728,742),
9.57 g—of triethylamine,
7.78 g—of acryloyl chloride and
60.0 g—of toluene
are reacted by the process indicated in Example 1.

After rectification at 176°-180° C. and 53 Pa, 30.8 g of the crude product give 17.02 g (57.4% of theory) of the acrylate in the form of a pale yellow oil, η$_{25}$=440 mPa.s.

| Elementary analysis | calculated for C$_{19}$H$_{23}$NO$_5$: | found |
|---|---|---|
| % C: | 66.07 | 65.10 |
| % H: | 6.71 | 6.89 |
| % N: | 4.06 | 4.19 |

-continued

| Elementary analysis | calculated for $C_{19}H_{23}NO_5$: | found |
|---|---|---|
| $M_n$: | 345 | 383 (GPC in THF) |
| $n_{25} =$ | | 1.5189 |
| Heat of polymerization: | 306.56 J/g | |
| Reaction maxima: | 195.4° C. | |
| | 258.7° C. | |
| | 303° C. | |

$T_G$ after polymerization for 6 hours at 250° C.: 167° C.

Example 8

Allylbicyclo[2.2.1]hept-5-ene-2,3-dicarboxylic acid N-(4'-acryloyloxycyclohexyl)-imide 150.5 g—of allylbicyclo[2.2.1]hept-5-ene-2,3-dicarboxylic acid N-(4'-hydroxycyclohexyl)-imide (prepared by reacting allylbicyclo[2.2.1]hept-5-ene-2,3-dicarboxylic anhydride with 4-aminocyclohexanol in accordance with the general instructions of U.S. Pat. No. 4,728,742) and 55.7 g—of triethylamine are dissolved in 500 g of toluene and cooled to 5° C. 45.25 g of acryloyl chloride are added dropwise slowly. The reaction of the educts and the working up are carried out as described in Example 1. This gives 89 g (50.2% of theory) of a clear, yellow, viscous resin.

| Analysis: | calculated for $C_{21}H_{25}NO_4$: | found |
|---|---|---|
| % C: | 70.96 | 71.14 |
| % H: | 7.09 | 7.21 |
| % N: | 3.94 | 3.65 |
| $\eta_{80°\,C.}$: | 908 mPa · s | |

USE EXAMPLES

Example A1

A mixture of 1 part of allylbicyclo[2.2.1]hept-5-ene-2,3-dicarboxylic acid N-(2'-acryloyloxyethyl)-imide (prepared as in Example 1) and 0.03 parts of benzildimethylketal is applied as a layer 12 μm thick to a copper-coated laminate. The layer is exposed to a 5 kW metal halide lamp, through a negative, for 2 minutes from a distance of 75 cm. Development in toluene gives a negative image. Thermogravimetric analysis of the image, i.e. the cured material, under nitrogen shows that loss in weight begins at 395° C.

Example A2

Example A1 is repeated, with the exception that, after the image has been developed, it is heated at 150° C. for 2 hours. Thermogravimetric analysis of the image under nitrogen shows that loss in weight begins at 415° C.

Example A3

A mixture of 1 part of the product according to Example 1, 0.03 part of 1-hydroxycyclohexyl phenyl ketone and 0.05 part of allylbicyclo[2.2.1]hept-5-ene-2,3-dicarboxylic acid N-benzenesulfonyloxyimide (prepared as in Example 1 of U.S. Pat. No. 4,709,047) is applied as a layer 12 μm thick to a copper-coated laminate. The layer is exposed to a 5 kW metal halide lamp, through a negative, for 3 minutes from a distance of 75 cm. Development in toluene gives a negative image. The developed image is then heated at 150° C. for 2 hours. Thermogravimetric analysis of the image under nitrogen shows that loss in weight begins at 430° C.

Example A4

A mixture of 1 part of the product according to Example 1, 2 parts of bis-[4-(allylbicyclo[2.2.1]hept-5-ene-2,3-dicarboxyimidophenyl)]-methane (prepared as in Example 11 of U.S. Pat. No. 4,515,962) and 0.03 part of 2-methyl-1-[4-(methylthio)phenyl]-2-morpholinopropan-1-one is dissolved in 2 parts of dimethylformamide. The solution is applied as a layer 12 μm thick to a copper-coated laminate and is dried for 5 minutes at 110° C., in the course of which a tack-free film is formed. The film is exposed to a 5 kW metal halide lamp, through a negative, for 2 minutes from a distance of 75 cm. Development in ethanol gives a negative image. The developed image is then heated at 150° C. for 2 hours. Thermogravimetric analysis of the image under nitrogen shows that loss in weight begins at 180° C. (less than 10% by weight; evaporation of the residual dimethylformamide solvent) and at 405° C.

Example A5

A mixture of 1 part of the product according to Example 1, 2 parts of bis-[4-(allylbicyclo[2.2.1]hept-5-ene-2,3-dicarboxyimidophenyl)]-methane (prepared as in Example 11 of U.S. Pat. No. 4,515,962), 0.03 part of 2-methyl-1-[4-(methylthio)phenyl]-2-morpholinopropan-1-one and 0.15 part of allylbicyclo[2.2.1]hept-5-ene-2,3-dicarboxylic acid N-benzenesulfonyloxyimide (prepared as in Example 1 of U.S. Pat. No. 4,709,047) is dissolved in 2 parts of dimethylformamide. A layer of this solution, 12 μm thick, is applied to a copper-coated laminate and is dried at 110° C. for 5 minutes, in the course of which a tack-free film is formed. The film is exposed to a 5 kW metal halide lamp, through a negative, for 5 minutes from a distance of 75 cm. Development in ethanol gives a negative image. The developed image is then heated at 150° C. for 2 hours. Thermogravimetric analysis of the image under nitrogen shows that loss in weight begins at 180° C. (less than 10% by weight; evaporation of the residual dimethylformamide solvent) and at 405° C.

Example A6

A mixture of 1 part of the product according to Example 1,2 parts of the reaction product of a so-called advanced epoxy resin based on bisphenol A (epoxide number 1.55 equivalents/kg) with acrylic acid, and 0.06 part of benzildimethylketal is dissolved in 2 parts of cyclohexanone. A layer of this solution, 24 μm thick, is applied to a copper-coated laminate and is dried at 110° C. for 5 minutes, in the course of which a tack-free film is formed. This film is exposed to a 5 kW metal halide lamp, through a negative, for 2 minutes from a distance of 75 cm. Development in 1,1,1-trichloroethane gives a negative image. The developed image is then heated at 150° C. for 2 hours. Thermogravimetric analysis of the image under nitrogen shows that loss in weight begins at 375° C.

Example A7

A mixture of 12 parts of the product according to Example 1,2 parts of the reaction product, described in Example A6, of an epoxy resin with acrylic acid, 0.06 part of benzildimethylketal and 0.05 part of allylbicyclo[2.2.1]hept-5-ene-2,3-dicarboxylic acid N-benzenesulfonyloxyimide (prepared as in Example 1 of U.S. Pat. No. 4,709,047) is dissolved in 2 parts of cyclohexanone. A layer of this solution, 24 μm thick, is applied to a copper-coated laminate and is dried at 110° C. for 5 minutes, in the course of which a tack-free film is formed. This film is exposed to a 5 KW metal halide lamp, through a negative, for 2 minutes from a distance of 75 cm. Development in 1,1,1-trichloroethane gives a negative image. The developed image is then heated at 150° C. for 2 hours. Thermogravimetric analysis of the image under nitrogen shows that loss in weight begins at 385° C.

Example A8

The product according to Example 8 is cast in a mould and is cured for 3 hours at 80° C., 2 hours at 150° C., 2 hours at 180° C., 2 hours at 220° C. and 10 hours at 250° C. The crosslinked polymer has the following properties:

$T_g$ (TMA): 354° C.

Flexural strength (ISO 178): 55.3 N/mm$^2$

Outer fibre elongation (ISO 178): 1.69%

Impact strength (ISO 179): 2.88 kJ/m$^2$

What is claimed is:

1. An imide of the formula I

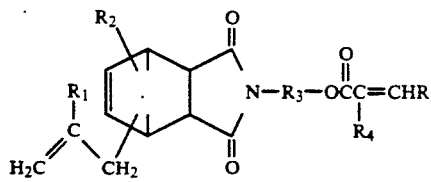

wherein $R_1$, $R_2$, $R_4$ and $R_5$ are each hydrogen and $R_3$ is 1,4-phenylene.

2. An imide of the formula I

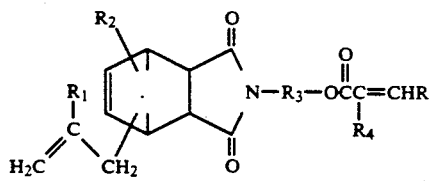

wherein $R_1$, $R_2$, $R_4$ and $R_5$ are each hydrogen and $R_3$ is —CH$_2$CH$_2$OCH$_2$CH$_2$—.

3. An imide of the formula I

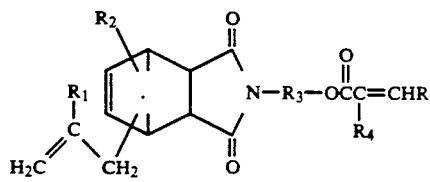

wherein $R_1$, $R_2$, $R_4$ and $R_5$ are each hydrogen and $R_3$ is 1,4-cyclohexylene.

* * * * *